United States Patent [19]

Barker et al.

[11] Patent Number: 4,755,649

[45] Date of Patent: Jul. 5, 1988

[54] APPARATUS FOR COMPRESSION WELDING OF ADAPTER AND FLANGED CATHETER

[75] Inventors: Reese H. Barker, Ogden; Victor L. Bartholomew, Sandy, both of Utah

[73] Assignee: Becton Dickinson and Company, Franklin Lakes, N.J.

[21] Appl. No.: 887,008

[22] Filed: Jul. 16, 1986

[51] Int. Cl.⁴ .............................................. H05B 6/54
[52] U.S. Cl. .............................. 219/10.81; 219/10.53; 604/283; 156/380.2
[58] Field of Search .................. 219/10.53, 10.81, 9.5, 219/85 R, 85 A, 8.5; 156/380.2, 380.3, 380.4, 380.1, 272.2, 273.7, 273.9; 604/283, 280

[56] References Cited

U.S. PATENT DOCUMENTS

| | | | |
|---|---|---|---|
| 3,322,590 | 5/1967 | Clark | 156/273.7 |
| 4,210,479 | 7/1980 | Fabisiewicz | 219/10.81 X |
| 4,419,095 | 12/1983 | Nebergall et al. | 219/10.53 X |
| 4,430,083 | 2/1984 | Ganz et al. | 604/283 |
| 4,574,173 | 3/1986 | Bennett | 219/10.53 |

*Primary Examiner*—Philip H. Leung
*Attorney, Agent, or Firm*—Aaron Passman

[57] ABSTRACT

A probe with a shoulder is used to support a pre-flanged distal end of a catheter placed inside of an adapter. The probe has a minor diameter to engage coaxially the bore of the catheter and a major diameter to carry coaxially the adapter in axial alignment with the catheter. The pre-flanged distal end of the catheter is compressed by the shoulder into the adapter during a dielectric welding operation as the probe is urged axially against the flange of the catheter. A support associated with the probe resists axial movement of the adapter and receives dielectric energy from the probe.

2 Claims, 2 Drawing Sheets

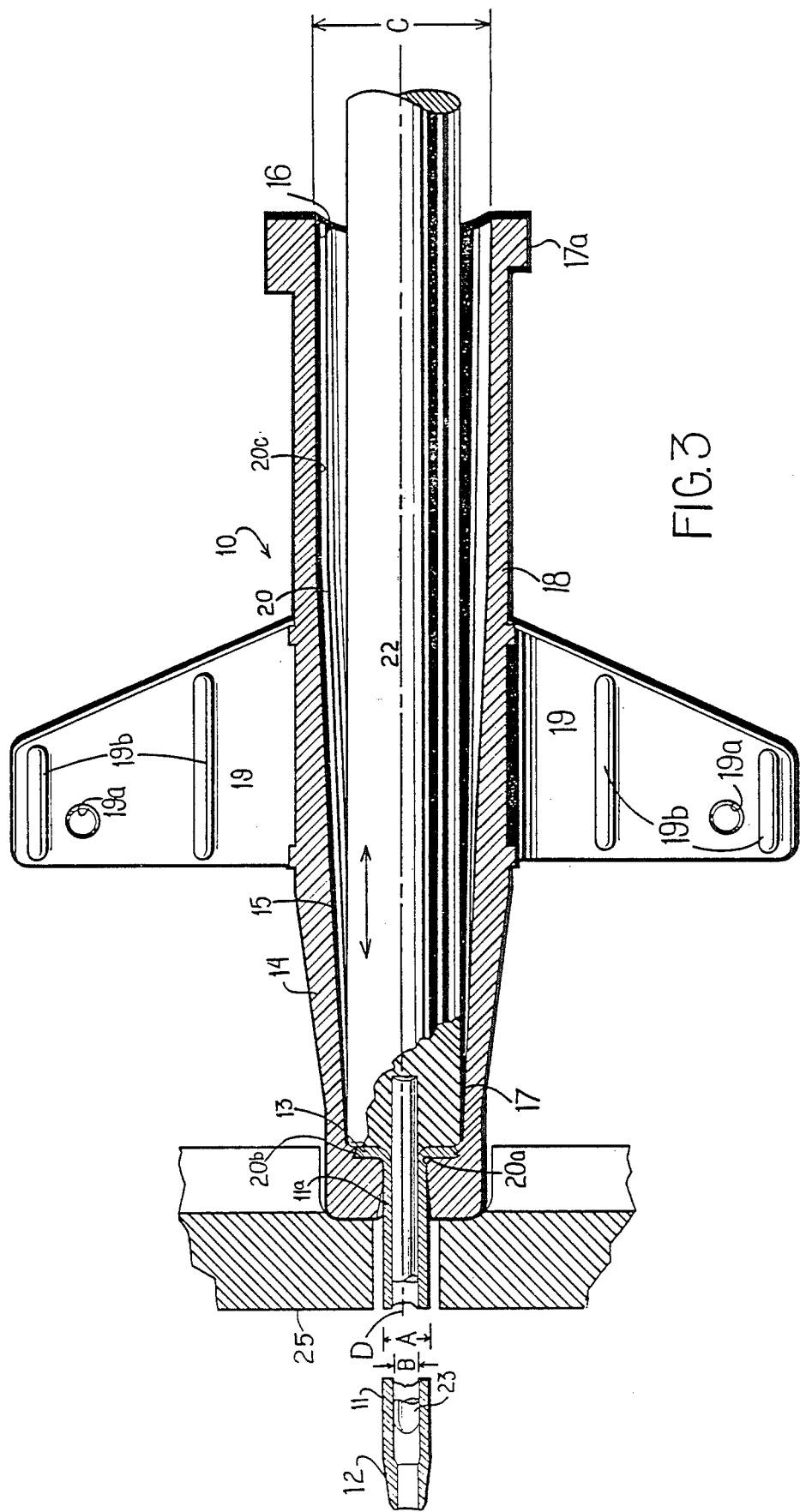

APPARATUS FOR COMPRESSION WELDING OF ADAPTER AND FLANGED CATHETER

BACKGROUND OF THE INVENTION

This invention relates to the connection between the thin-walled small diameter catheter for insertion into the lumen of a human and its respective attachment adapter which has a larger inside diameter and is made to connect to the supply for the administration fluid. More specifically, it relates to a unique product resulting by the assembly of these two components forming a fluid tight connection to prevent leakage of the flow of fluid through the adapter and into the catheter.

Prior patents have disclosed techniques for connecting catheter tubing to adapters. One such patent, U.S. Pat. No. 4,354,495, shows an injection molding operation which is used to attach the hub to the catheter. The distal end of the catheter has a thread-like configuration induced by heating and swelling the catheter at its distal end to form the helix of the thread. This thread-like member is used as a situs about which the injection molded hub can adhere. This connection is primarily mechanical. The internal juncture in the bore and between the distal end of the catheter and the proximal end of the hub are not welded and do not form a fused bond at the transition for the flow of the administrated fluid from the hub to the catheter.

U.S. Pat. No. 4,177,809 shows a three-piece configuration for mounting the catheter to the hub. The distal end of the catheter is surrounded by a funnel-shaped wedge inserted between it and the inside diameter of the hub to act as a key or keeper to retain the catheter relative to the hub in its axial position. This force fit is merely mechanical. Even though the wedge has a funnel-like interior, there is still a shoulder between it and the inside diameter of the hub and there is absolutely no teaching of pre-flanging and welding.

U.S. Pat. No. 3,720,210 shows a way of preparing the distal end of the catheter with a curl in order to form a place at which an insert molded hub can be affixed without concern for the two separating from one another. The connection is mechanical.

U.S. Pat. No. 4,419,095 discloses RF heating to butt weld the ends of two tubes together. The outside mandrel has a convex surface in order to allow air to escape therefrom during welding. There is also a recess along the outside wall of an end of one of the tubes in order to facilitate the removal of air. The inside mandrel has an insulated sleeve over it to facilitate the weld and prevent the inside of the tube from sticking to the inside mandrel. There is absolutely no teaching of welding a small pre-flanged tube into the inside end cavity of a larger hub with heat caused by dielectric energy. The '095 process is merely designed to melt the tubing at the abutted interface.

U.S. Pat. No. 3,966,520 shows ultrasonic welding as opposed to RF welding wherein a conically-shaped tool surrounds the ends of one tube that extends over in a lap joint about another tube. Ultrasonic vibrations in the frequency range of 20 to 40 kHz are used during swaging the outer tube toward the underlapping inner tube and in doing so tends to chamfer the leading end of the outer overlapping tube. The internal juncture between the tubes still has a shoulder; there is no teaching of welding a much smaller catheter to the inside end of a larger hub with a bonding and forming operation.

U.S. Pat. No 4,430,083 is typical of state of the art prior patents in that it shows a catheter receiving hub wherein there is an enlarged recess to receive the catheter such that the flow through the inside of the passageway through the tube is uniform. This requires that the hub be molded from both directions and a split set of core pins be used. This approach, while possible, does not afford the best possible fused junction between the hub inside diameter passage and the thin walled small catheter bore.

Therefore, it is an object of the present invention to provide a juncture between the hub and the catheter which forms a fused, flanged transition from the larger inside diameter of the adapter to the smaller inside bore of the thin walled catheter such that the integrity of the bond and the ultimate safety for the patient on which the combination is used will be excellent.

It is a further object of the present invention and the preferred embodiment to disclose a quick, efficient means by which the distal end of the thin walled catheter and the inside of the proximal end of the adapter can be joined together using a simple welding apparatus to leave a clean internal connection therebetween without any adhesives, flash from molding operations or additional component parts to wedge and force-fit the two together.

Consistent with the foregoing objects and in order to overcome the problems besetting the prior art, the present disclosure which follows seeks to disclose and explain a preferred embodiment in which the connection between the distal end of the catheter and the proximal end of the hub form a clean, continuous fluid tight internal junction having a fused transition from the larger diameter of the inside of the adapter to the smaller diameter of the inside of the thin walled catheter.

SUMMARY OF THE INVENTION

The relatively simple and desired result of a technique, product and method for joining a elongated, thin-walled, hollow, tubular catheter having a taper at its proximal end and being flanged at its distal end to the inside end of an adapter for facilitating connection of the catheter to an administration set is disclosed. More specifically, the adapter has a relatively thick wall tubular body with an internal chamber tapering from a larger diameter at the distal end to a smaller internal diameter at the proximal end which internal diameter thereat is approximately equal to the outer diameter of the distal end of the catheter. Proximal and distal are used here in relation to the patient. The tapered hollow chamber within the adapter has a portion for receiving the distal end of the catheter during a welding operation. Prior to assembly of the adapter and catheter, a rotating fixture holds the catheter with its distal end extended toward a hot air blast which softens the plastic and permits the end to bend outwardly to form a flange. The flanged catheter is then coaxially placed upon a probe which has a minor diameter and a major diameter with a shoulder transition therebetween. The catheter is slid coaxially about the minor diameter of the probe with its distal end biased toward the shouldered transition. Over the catheter and coaxially thereabout is placed an adapter centered upon the major diameter of the probe and in coaxial alignment with the catheter such that the inside of the proximal end of the adapter abuts the pre-flanged proximal end of the catheter as same rests against the shouldered transition of the probe. The catheter being biased against the shouldered transition, the adapter being located and held relative to the distal flanged end of the catheter and the probe being urged toward the catheter whereby the pre-flanged portion of the catheter at its distal end is forced into the proximal end wall of the chamber of the adapter as dielectric energy is applied causing the polymeric material of the catheter flange and hub to melt, weld, and fuse under the heat and load generated. The pressure of the probe, the biasing of the catheter, and the positioning of the adapter cause the catheter material to compress and intimately fuse with the internal proximal end material of the adapter chamber. This compression fusing process forms a smooth end wall connection at the junction of the distal end of the catheter where same meets the proximal end of the adapter chamber providing a fluid tight transition from the large inside hollow of the adapter chamber of the hub into the smaller inner diameter of the catheter bore.

The resulting product is a relatively thick-walled sturdy adapter which is easy to handle and connect an administration set with a fluid-tight, connection leading into a securely attached relatively thin wall and much smaller catheter bore. There are no extraneous adhesives, cements or bonding agents between the catheter and the hub at and around the juncture. In addition, there are no areas of flash due to the unique nature of the di-electric welding and compression molding operation.

BRIEF DESCRIPTION OF THE DRAWINGS

FIG. 3 is a plan view mostly in cross-section of the adapter and probe used to dielectrically weld with compression the flanged transition between the thin walled catheter and the thick walled adapter.

DETAILED DESCRIPTION OF THE DRAWINGS

Figure 2:
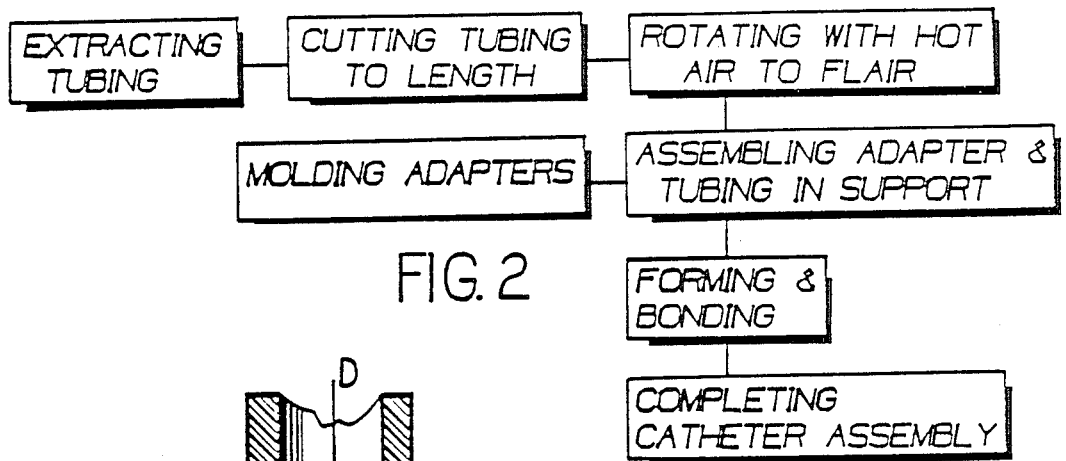
FIG. 2 is a block flow diagram showing the steps of the preferred process for making the preferred assembly of end adapter and flanged catheter.

Turning now to the figures and more specifically to FIG. 3, there is shown the finished product, that is the di-electrically welded catheter and adapter combination 10. The catheter 11 has a tapered proximal end 12 and a pre-flanged distal end 13 with a catheter 11 outer diameter A and an inner or bore diameter B. In combination with the catheter 11 is the adapter 14 which includes tapered internal chamber 15 that extends from the distal end 16 to the proximal end 17 and reduces from a larger diameter C to a smaller diameter which is the same as A, the outer diameter of the catheter 11.

The adapter 14 has a number of features which are incorporated to facilitate its use in connection to an administration set such as the luer thread 17a, the outer body wall 18, and the tie-down wings 19 which include suturing holes 19a and reinforcing ribs 19b. Each wing 19 extends transverse to the axis of the adapter designated D in FIGS. 1 and 3. The internal wall 20 of chamber 15 has a proximal end portion with a bore having the diameter A for receiving the distal end 11a of the catheter 11. Extending distally from end portion 20a is a first radially extending end wall chamber portion 20b which acts as the major part of the transition from diameter A toward larger internal distal diameter C. Wall portion 20b extends radially to the tapered inside chamber wall 20c angled relative to the axis D to open chamber 15 to diameter C at the distal end opening of the hub 14. Consequently, the chamber 15 is formed of three areas defined by walls 20a, 20b, and 20c extending from a minor proximal inside diameter A to a major distal inside diameter C.

The catheter 11 can have a variety of internal diameters which, for example, could extend from 0.017 to 0.0482 inches depending on the particular gauge and length of the catheter. The outer diameters all tend to be about the same for any given gauge and the wall thickness of the catheter tends to vary from 0.003 to 0.009 inches. Similarly, the adapter 14 has a varying dimension for diameter A as a function of the particular gauge catheter which is inserted through end portion 20a. The slight taper extending distally from end wall 20b to the end of adapter 14 is merely for the ease of molding the adapter. It should be noted, however, that the relative end wall thickness at 20b of the adapter 14 about the area of the catheter 11 at 11a is generally three to four times that of the wall thickness of the catheter 11 such that the dielectric field is applied in such a way that these materials of different mass and relative thickness are melted uniformly and equally at their interface to generate the desired smooth flanged fluid tight juncture generally shown in the area 21 in FIG. 1. The heavier thicker end wall 20b acts as a support for the pre-flanged end 13 of the catheter 11 during the assembly operation.

The preferred polymer for the catheter and the adapter 14 is a highly responsive material to the passage therethrough of di-electric energy such that the force and energy across the juncture at area 21 is efficiently used. The di-electric welding with compression is a process wherein voltage in the range of 1000 volts and with a frequency range of 6 MHZ to 100 MHZ is used to heat the molecules at the interface of 20b and 13 in such a fashion that the material melts. Pressure permits movement of polymer across the interface. This process is localized at the interface and thus efficiently used for joining the relatively thin pre-flange 13 and the relatively thick end wall 20b. Consequently, a smooth juncture at area 21 is created with a strong bond therebetween see FIG. 1. In particular, the flange 13 becomes inset into wall 20b of the adapter 14. The flange 13 does not thin during dielectric welding with compression.

In the preferred embodiment, and for purposes of biocompatibility in a medical device for use in connection with the human blood vessels, polyurethane is the preferred choice and more specifically, the pure polyurethane produced under the trademark Vialon ® by Deseret Medical, Inc., Sandy, Utah. This material has been found to adapt well to the combined di-electric welding under compression operation described. The material difference between the catheter 11 material and the adapter 14 is that the former may include a radiopaque stripe of barium sulphate, but the latter does not. The addition of the radiopaque stripe does not affect the ability to obtain a smooth, strong fused juncture at area 21. One reason for this is the care with which the radiopaque stripe has been buried within the basic polymeric, polyurethane Vialon ® material used to form the catheter tubing. That is to say that, there is sufficient Vialon polyurethane covering the stripe and available to form the juncture notwithstanding the addition of the radiopaque stripe.

Turning now to FIG. 3, there is shown the elongated probe 22 used to support, hold and form the juncture at area 21 between the catheter 11 and the body of the adapter 14. The catheter end portion 23 of the probe 22 has an outer diameter of approximately B such that the catheter 11 can be coaxially positioned thereabout during the di-electric welding with compression operation. The length of portion 23 is, of course, a function of the particular catheter length and is also a function of the diameter B. More distal than portion 23 is a transition shoulder portion 24 which is essentially at a right angle relative to the axis D, see FIG. 1. Shoulder portion 24 extends the diameter B radially outwardly to a distance which is slightly less than the radial extent of inside wall 20b of adapter chamber 15. The catheter 11 in the area of 11a need not touch the open distal end of adapter 14 because during the di-electric welding under compression the bond is axial being between the interface at 13 and 20b. Intimate contact between the catheter 11 and the adapter 14 are essential for forming a complete and liquid-tight bond and the compression applied by the probe 22 via shoulder portion 24 is resisted by an external support 25, see FIG. 3. The corner 26 formed between the outer radial extent of shoulder portion 24 and the outer cylindrical 22a surface of probe 22 engages the proximal inside of chamber 15 of the adapter 14 and holds same coaxial with respect to the axis D.

Figure 4:
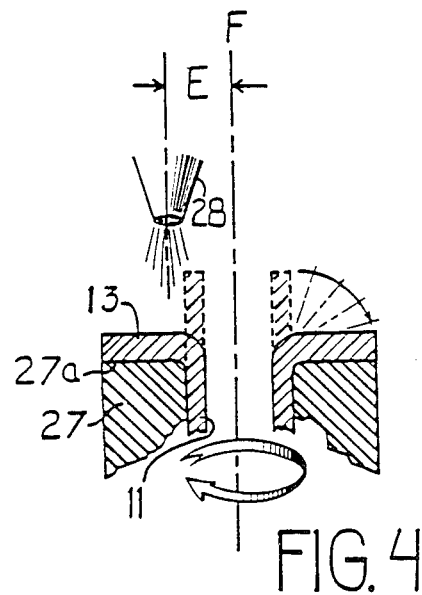
FIG. 4 shows a partial cross-sectional view of the arrangement used to pre-flange the catheter.

In FIG. 4 there is shown an enlarged partial view in cross section of the tool used to pre-flange the catheter end 13. Most simply the tool is in the form of a rotary collet 27 which rotates at a speed of approximately 20 RPM and holds the distal end of the catheter 11 to be flanged extending slightly beyond the face 27a of the collet 27. The catheter end is subjected to a hot air blast from nozzle 28 which is offset a distance E from the axis F of the collet 27. The hot air blast from nozzle 28 tends to soften the extended end of the catheter 11 causing same to droop or bloom like a flower outwardly and a downwardly toward the face 27a of the collet 27, see FIG. 4. The extended catheter end is shown in broken lines and the flanged-over end is shown in solid lines. Note that once flanged, the wall thickness of the flange is greater than the wall thickness of the catheter 11. There is a tendency of the catheter to relax upon softening as a consequence of the draw down ratio which is a function of the extrusion process by which the tubing was made. The temperature of the hot air blast has to be sufficiently hot and strong to soften the catheter tubing. The rotation helps to uniformly distribute the heat and force of the hot air blast, and the offset positioning of the nozzle helps to flatten the flanged end 13 against the face 27a of the collet 27. That face 27a helps cooling of the flanged catheter end because the heat is quickly removed. This flanged end is then used to form the adjoining surface with the end wall 20b of the adapter 14 as herein described.

Therefore, during assembly the catheter 11 is inserted over the probe 22 first engaging end 23 and extending thereover such that pre-flanged portion 13 bears against transition shoulder 24. Thereover and about the distal end of catheter 11, is placed the adapter 14 with its larger open end 16 first slid over the catheter 11 until the portion near proximal end 17 engages about the outer diameter A of the catheter 11, and more specifically, the surfaces 13 and 20b are brought axial into engagement. The probe 22 is biased into the catheter 11 as shown by the arrow in FIG. 3, and the adapter 14 is held distally against the catheter 11 causing the pre-flanged area 13 on the catheter 11 to be held tightly against the inside end wall 20b of the adapter 14. Di-electric energy is then passed through the probe 22 across the juncture 21 of the catheter 11 and the adapter 14 into the external support 25 causing the juncture 21 at their interface. The flange 13 radially extrudes at its radial extend becoming flush with end wall 20b.

Figure 1:
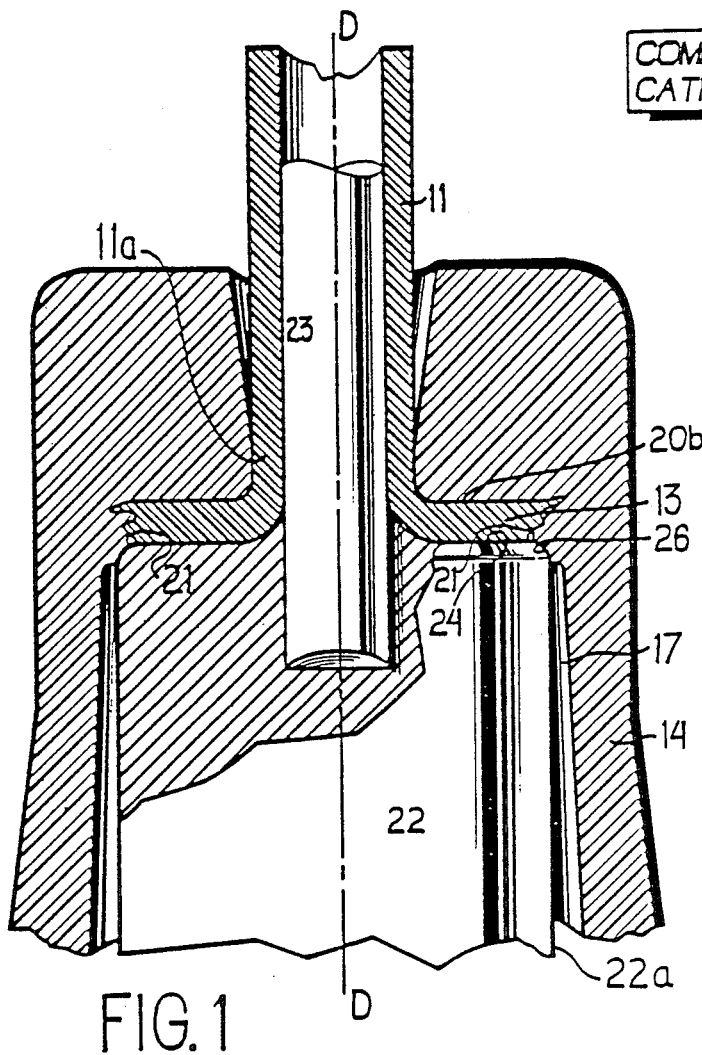
FIG. 1 is an enlarged partial view in cross-section of the juncture between the catheter and the adapter showing the nature of the flanged transition formed at the distal end of the catheter where same is di-electrically welded with compression and thereby fused into the proximal end wall of the adapter chamber.

Turning now to FIG. 1, there is shown the area of the fused juncture 21 between the adapter 14 and the catheter 11 and more specifically, the way in which the catheter material compression and heat forms a fluid tight transition between the thick walled large diameter adapter chamber 15 end the thin walled small bore catheter 11.

Those skilled in the art no doubt appreciate that changes in the flange, size, shape and position, the relative size of the components, the materials and other dimensional and detail specifics of the configuration can be made without departing from the scope of the invention which is defined in the claims which follow.

What is claimed:

1. A dielectric welding apparatus for use in coaxially supporting a catheter and its adapter about an axis during an operation for connecting the bore of the catheter to the inside of the adapter to form a flanged juncture from the larger internal diameter of the adapter to the smaller internal diameter of the catheter bore wherein the apparatus comprises:

an elongated probe located along the axis and having a minor diameter at its proximal end for carrying the catheter along the axis and a major diameter at its distal end for carrying the adapter in axial alignment with the catheter;

a shoulder portion on said elongated probe disposed between said minor diameter and said major diameter with a radially extending part thereof as a transition outwardly of said minor diameter toward said major diameter for engaging a pre-flanged distal end on the catheter when it is placed axially over said minor diameter and urged axially by said radially extending part, and said major diameter having an axial extent sufficient for cooperating with the inside of the adapter when the adapter is coaxially positioned about the catheter distal end to align axially the adapter with respect to the catheter forming an interface between at least the pre-flanged distal end on the catheter and the inside end wall of the adapter, and an external support about the adapter when positioned on said probe to receive dielectric energy across the interface between catheter and adapter and to carry and axially align the adapter as said probe urges the catheter pre-flanged distal end into the inside wall of the adapter.

2. The apparatus of claim 1 wherein said portion of said elongated probe includes a corner between the outer radial extent of said shoulder portion and said major diameter for engaging the proximal inside of the adapter to thereby coaxially holding the adapter relative to the axis.

* * * * *